(12) United States Patent
Kaltenbeck et al.

(10) Patent No.: US 7,807,041 B2
(45) Date of Patent: Oct. 5, 2010

(54) METHOD FOR DETECTING THE PRESENCE OR ABSENCE OF A GAS BUBBLE IN AN AQUEOUS LIQUID

(75) Inventors: Heinz Kaltenbeck, Graz (AT); Robert Grübler, Graz (AT); Egon Landschützer, Graz (AT)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1289 days.

(21) Appl. No.: 11/216,743

(22) Filed: Aug. 31, 2005

(65) Prior Publication Data

US 2006/0042963 A1    Mar. 2, 2006

(30) Foreign Application Priority Data

Sep. 2, 2004    (AT)    .............................. A 1467/2004

(51) Int. Cl.
*G01N 27/407*    (2006.01)
(52) U.S. Cl. ...................... 205/775; 205/782; 204/431
(58) Field of Classification Search .................. 205/775, 205/779, 785.5, 792, 783, 782; 204/409, 204/431, 432, 400–435
See application file for complete search history.

(56) References Cited

U.S. PATENT DOCUMENTS

| 3,874,850 A | 4/1975 | Sorensen et al. |
| 3,961,898 A | 6/1976 | Neeley et al. |
| 4,358,423 A | 11/1982 | Nedetzky |

(Continued)

FOREIGN PATENT DOCUMENTS

EP    0 484 876 B1    7/1997

(Continued)

OTHER PUBLICATIONS

Linek, V., Vacek, V., Sinkule, J., Benes, P., "Measurement of Oxygen by Membrane-Covered Probes: Guidelines for Applications in Chemical and Biochemical Engineering", Ellis Horwood Limited, 1988, pp. 91-93.

(Continued)

*Primary Examiner*—Nam X Nguyen
*Assistant Examiner*—Gurpreet Kaur
(74) *Attorney, Agent, or Firm*—Thomas E. Lees, LLC

(57) ABSTRACT

A method for detecting the presence or absence of a gas bubble in an aqueous liquid is provided comprising providing an amperometric sensor positioned within a measuring chamber, wherein the amperometric sensor is configured to determine the concentration of a gaseous component dissolved in a liquid, the amperometric sensor comprising a sensitive region; positioning the liquid in the measuring chamber; taking at least one first measurement value of the gaseous component from a first portion of the liquid after a predetermined response time, the first portion located in the sensitive region of the sensor; moving the liquid along in the measuring chamber, such that a second portion of the liquid, which had previously been located outside the sensitive region of the amperometric sensor, is positioned in the sensitive region; taking at least one second measurement value of the gaseous component from the second portion of the liquid; and detecting the presence or absence of a gas bubble by comparing the first and second measured values. The gas bubble, if present, is in at least partial contact with the sensitive region of the amperometric sensor.

18 Claims, 2 Drawing Sheets

U.S. PATENT DOCUMENTS

| | | | |
|---|---|---|---|
| 6,773,577 B1 | 8/2004 | Broy et al. | |
| 7,084,646 B2 * | 8/2006 | Gruebler et al. | 324/693 |
| 7,297,241 B2 * | 11/2007 | Kontschieder et al. | 204/403.01 |
| 2003/0080002 A1 * | 5/2003 | Taagaard et al. | 205/782 |

FOREIGN PATENT DOCUMENTS

| | | |
|---|---|---|
| EP | 1 394 534 A2 | 3/2004 |
| EP | 1 505 381 A | 2/2005 |
| WO | WO 01/33195 A1 | 5/2001 |

OTHER PUBLICATIONS

Ateya, D.A. et al., "Impedance-based response of an electrolytic gas bubble to pressure in microfluidic channels", Sensors and Actuators A, Elsevier Sequoia S.A., Lausanne, Ch. Bd. 122, Nr. 2, Aug. 26, 2005, pp. 235-241.

Park, J. et al., "A Simple on-chip self-diagnosis/self-calibration method of oxygen microsensor using electrochemically generated bubbles", Sensors and Actuators B, Elsevier Sequoia S.A., Lausanne, Ch, Bd. 108, Nr. 1-2, 22. Jul. 2005, pp. 633-638.

Maisonhaute, E. et al., "Microelectrode study of single cavitational bubbles induced by 500 kHz ultrasound", Ultrasonics: Sonochemistry, Butterworth-Heinemann, GB, Bd. 9, Nr. 5, Oct. 2002, pp. 275-283.

* cited by examiner

METHOD FOR DETECTING THE PRESENCE OR ABSENCE OF A GAS BUBBLE IN AN AQUEOUS LIQUID

CROSS-REFERENCE TO RELATED APPLICATION

This application claims priority to Austrian patent application no. A 1467/2004 filed 2 Sep. 2004, the disclosure of which is incorporated herein by reference.

BACKGROUND OF THE INVENTION

The present invention relates to analysis systems and methods thereof, and in particular to a method for detecting the presence or absence of a gas bubble in an aqueous liquid.

For the purposes of clinical diagnosis analyzing systems are used for blood-gas analysis or other measurements in liquid samples. Such systems are employed for instance for determining the partial oxygen or carbon dioxide pressure in blood, or the hemoglobin parameters of whole blood, and for measuring the pH-value or ion concentration or special metabolites.

Complex analysis systems of this kind are usually provided with different sensor elements for determination of the parameters of interest, which elements are used for a multitude of measurements. Such sensor elements are for instance electrochemical or optical sensors for determining gas values, pH, ion values or metabolite values, or optical measuring units for the determination of hemoglobin values.

In electrochemical gas sensors, also known as gas-selective or gas-sensitive electrodes, the gas molecules to be determined diffuse from an usually aqueous exterior solution or a gas phase into the interior electrolyte chamber of the sensor via a gas-permeable membrane which is essentially fluid- and ion-impermeable. In addition to a liquid or solid interior electrolyte layer, the interior electrolyte chamber contains electrodes for electrochemical determination of the gas, especially measuring or working electrodes, counter-electrodes and reference electrodes. In the interior electrolyte chamber the electrochemical reactions for determining the gas by means of amperometric methods take place.

A frequently used gas sensor is the Clark oxygen sensor, for instance, where a gas-permeable membrane separates the interior electrolyte solution from the aqueous exterior medium, i.e., the medium to be measured. In the simplest case two electrodes dip into the interior electrolyte solution, one of which is placed immediately behind the membrane as a working electrode. After a polarization voltage of suitable strength is applied, the oxygen which has diffused through the membrane from the measurement medium into the interior electrolyte chamber, is consumed by electrochemical reduction at the working electrode and an electric current corresponding to the substance consumed flows. This current is proportional to the partial pressure of oxygen in the medium to be measured and represents the primary measurement quantity.

Other frequently employed electrochemical gas sensors with gas-permeable membranes are electrochemical sensors for the measurement of hydrogen by means of oxidation on platinum electrodes, for instance.

Such electrochemical gas sensors are often used in medical and diagnostic analyzers for the determination of partial gas pressures or gas concentrations in liquids. In particular, they are employed in blood gas analyzers, which play an important role in medical diagnosis. Blood gas analyzers often are provided with a plurality of sensors for diverse parameters, which are arranged in series. The sample fluid flows through the measuring channel of a measurement chamber containing the sensors, measurement often being taken by the "stop-flow-method", i.e., with the sample at standstill during the actual measurement. Systems of this type are often used for routine measurements in clinics, laboratories and by medical practitioners, thus requiring the sensors used to have long service life, high accuracy and good reproducibility.

In the OMNI analyzer systems of Roche Diagnostics amperometric oxygen sensors are used for the determination of oxygen. These oxygen sensors are miniaturized gas sensors of the Clark type. Besides the actual sensor with its interior electrolytic chamber containing the electrodes, the gas sensor elements comprise a sample passage for the transport and intermediate storage of the sample. Between the interior electrolytic chamber and the sample passage there is a gas-permeable and essentially ion- and fluid-impermeable plastic membrane separating the interior electrolytic chamber from the sample passage. In that instance the membrane is provided in a mechanically stretched state.

Frequently, thin plastic membranes are employed in electrochemical gas sensors, with layer thicknesses in the micrometer range, which are made from hydrophobic plastic materials, especially from polytetrafluoroethylene, poly-propylene, or polyethylene. Further details concerning typical membrane materials may be found in "Measurement of Oxygen by Membrane-covered Probes" (Ellis Horwood series in analytical chemistry, 1988, Ellis Horwood Limited, page 91f).

When gaseous analytes are determined in aqueous solutions by means of electrochemical gas sensors, especially in physiological fluids such as whole blood, serum or urine, problems may occur in certain rare cases during sample measurement or during calibration or quality control, if the sample or the calibrating or control medium does not completely fill the sample passage, or if the solution contains gas bubbles, e.g., air bubbles, in the region of the sensors. Especially in blood-gas analyzer systems with sensor elements for small sample volumes gas bubbles may cause measurement errors, which will necessitate efficient checking for the presence or absence of gas bubbles in this case. Gas bubbles mostly adhere to the membrane surface. This phenomenon is observed when during the filling process of the sample passage the aqueous fluid avoids the hydrophobic surface of the membrane on one or both sides. If it is possible for the front of the fluid to laterally bypass the membrane before it is completely covered by the fluid, a gas bubble will form in the area of the membrane. Already existing as well as newly formed gas bubbles will mostly adhere to the membrane and often will not be removed by the fluid flow. A gas bubble adhering to the membrane or remaining in the immediate vicinity of the membrane will result in a measurement error, which will not be recognized as such without additional efforts to detect such bubbles.

The problem of enclosed air bubbles which cause measurement errors by impeding sufficient wetting of the surface of the sensors used is pointed out in the prior art. Measures for recognition of such errors will be necessary above all in automated analyzers, where the filling process of the measuring capillary or the absence of bubbles in the sample must be controlled automatically.

Certain known methods cannot efficiently detect air bubbles, however, which do not extend over the whole cross-section of the measuring passage or the measuring capillary. Resistance measurement would in such cases show slight variations in the measurement signal, which could not be discerned from variations in the signal caused by different conductivity of the individual samples due to differing hematocrit values, for instance.

SUMMARY OF THE INVENTION

It is against the above background that the present invention provides certain unobvious advantages and advancements over the prior art. In particular, the inventors have recognized a need for improvements in methods for detecting the presence or absence of a gas bubble in liquids.

Although the present invention is not limited to specific advantages or functionality, it is noted that the present invention provides a method for the detection of a gas bubble, which typically is in at least partial contact with the sensitive region of an amperometric sensor located in a measuring chamber, in such a way that even very small gas bubbles may be definitely detected without additions or changes to the measuring chamber, thus permitting the taking of suitable counter measures.

In accordance with one embodiment of the present invention, a method for detecting the presence or absence of a gas bubble in an aqueous liquid is provided comprising providing an amperometric sensor positioned within a measuring chamber, wherein the amperometric sensor is configured to determine the concentration of a gaseous component dissolved in a liquid, the amperometric sensor comprising a sensitive region; positioning the liquid in the measuring chamber; taking at least one first measurement value of the gaseous component from a first portion of the liquid after a predetermined response time, the first portion located in the sensitive region of the sensor; moving the liquid along in the measuring chamber, such that a second portion of the liquid, which had previously been located outside the sensitive region of the amperometric sensor, is positioned in the sensitive region; taking at least one second measurement value of the gaseous component from the second portion of the liquid; and detecting the presence or absence of a gas bubble by comparing the first and second measured values. The gas bubble, if present, is in at least partial contact with the sensitive region of the amperometric sensor.

In another typical embodiment of the present invention, the liquid may be inferred to be free of bubbles in the sensitive region of the amperometric sensor, if the second measured value is higher by a predetermined amount than the first measured value.

The method of the invention, in accordance with at least one embodiment, is based on the fact mentioned above, i.e., that amperometric gas sensors consume the analyte. It is assumed that the gas component to be determined by the amperometric sensor is also present in the gas bubble.

If, for instance, the liquid in the immediate vicinity of an amperometric $O_2$-sensor is free of gas bubbles containing $O_2$, the measuring process will in the course of time lead to a depletion of $O_2$ in the liquid in the immediate vicinity of the sensor due to the sensor consuming $O_2$, and thus the amperometric signal will decrease. If the liquid is now moved along the amperometric signal will increase again by a certain amount, but the increase will not occur if a gas bubble is present.

According to still another embodiment of the present invention, the second portion of the liquid may be moved to the sensitive region of the sensor in a measuring chamber with open inlet and outlet without significant change in pressure, typically by a pumping or suction device. Thus pressure loads on pressure sensitive components of the system (e.g., the sensor membranes) are avoided. Besides, the requirements concerning the sealing properties of the system are less strict.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following schematic drawings, where like structure is indicated with like reference numerals and in which.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiment(s) of the present invention.

DETAILED DESCRIPTION OF THE INVENTION

Figure 1A:
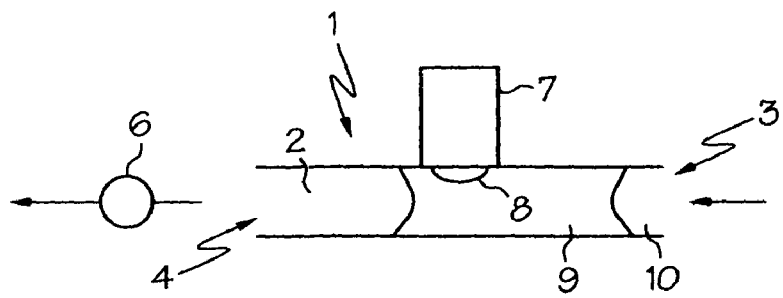
FIGS. 1a and 1b schematically show a measuring set-up in accordance with an embodiment of the present invention, with a bubble-free measuring liquid.
Figure 1B:
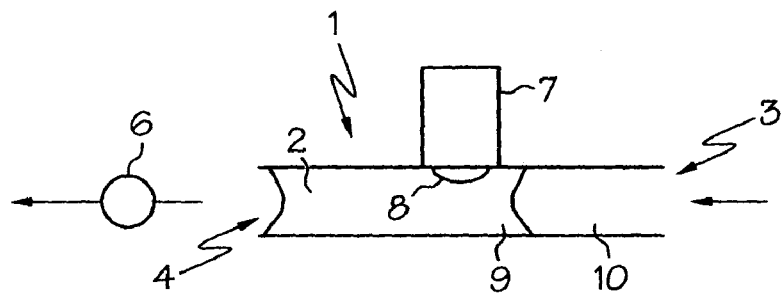

The measurement set-up schematically shown in FIGS. 1a, 1b has a measuring chamber 1 with a sample passage 2 extending over the whole length, whose inlet opening is indicated by 3. At the outlet opening 4 a pumping or suction device 6 is placed, for instance a peristaltic pump. The sample passage 2 may contain a plurality of different electrochemical sensors, but must have at least one amperometric sensor 7, for instance an $O_2$-sensor, whose sensitive region 8 protrudes into the sample passage 2 and into the measurement liquid 9 (e.g., a calibrating, control or sample fluid) contained therein. The measurement liquid 9 is separated by a separating gas bubble 10 from the subsequent liquid sample.

Figure 2A:
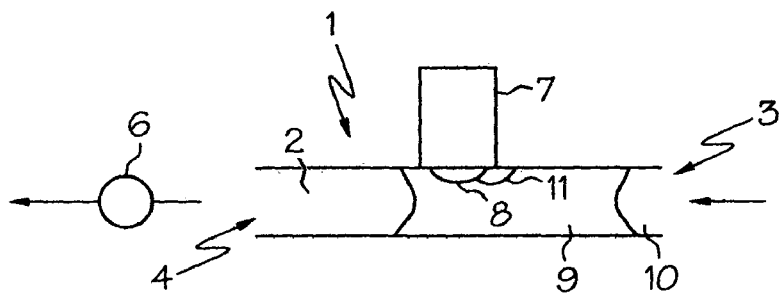
FIGS. 2a and 2b show the apparatus of FIGS. 1a, 1b with a gas bubble in the region of the amperometric sensor.
Figure 2B:
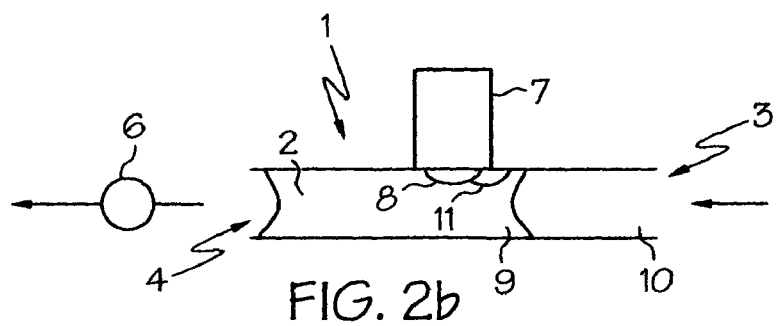

FIGS. 1a and 1b show the measurement situation without noxious gas bubble in the sensitive region 8 of the sensor 7. FIGS. 2a and 2b show the situation with a gas bubble 11 in at least partial contact with the sensitive region 8 of the amperometric sensor 7. In both cases the measurement liquid 9 may be moved, without significant pressure change in the liquid 9 itself, for instance by means of a pumping or suction device, from a first position (see FIGS. 1a resp. 2a) to a second position (see FIGS. 1b resp. 2b), in such a way that a second, unused portion of the liquid 9, which was previously held outside the sensitive region of the amperometric sensor, is now positioned in the sensitive region 8 of the amperometric sensor 7.

In the measurement situation as shown in FIGS. 2a and 2b it can be seen that the noxious gas or air bubble 11 does not move, although the liquid 9 moves towards the outlet opening 4, but adheres to the sensitive region of the sensor 8.

Figure 3:
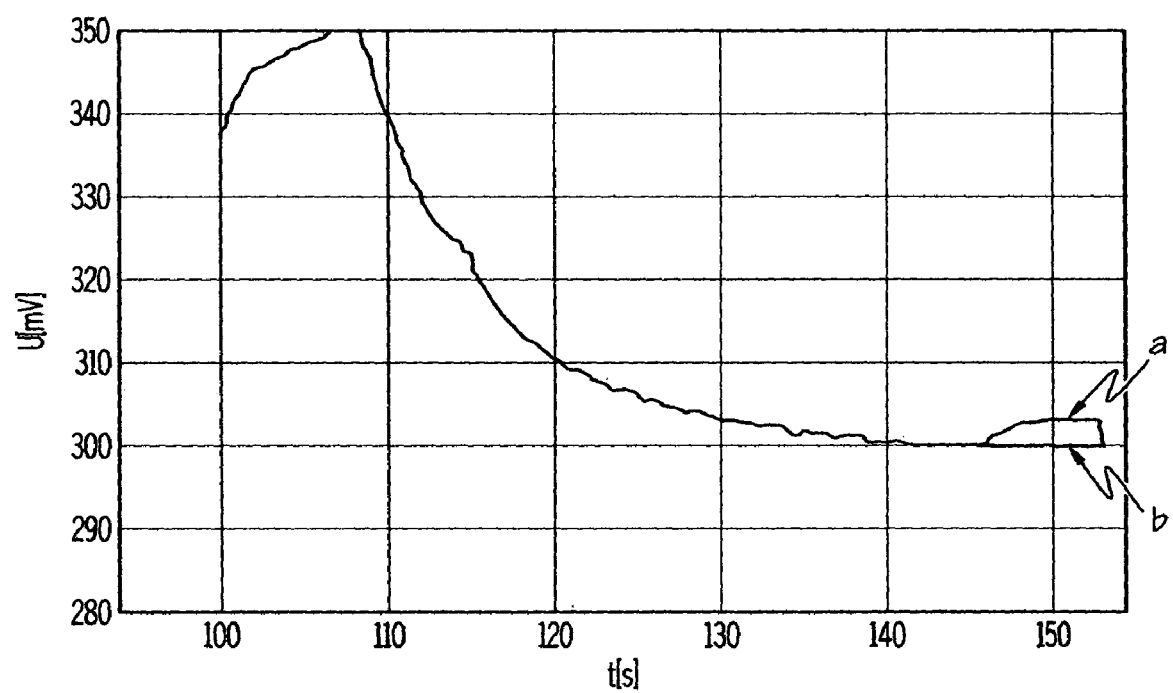
FIG. 3 shows the sensor signal over time in a measurement example.

In the measurement example shown in FIG. 3 the voltage U (in mV), which is proportional to the $O_2$-concentration in a liquid, e.g., a blood sample, is depicted as a function of time t (in s). The amperometric signal is passed to a current/voltage converter and measured as a voltage proportional to the current.

When, for instance, the liquid is introduced into the measurement chamber and the sensor signal is measured over time t, beginning immediately after the introduction of the liquid, the signal curve represents the superposition of two different processes: (1) the response of the sensor to the $O_2$-value of the liquid introduced, where the signal generated by this process decreases until equilibrium is reached, and (2) the inherent $O_2$-consumption of the amperometric $O_2$-sensor indicated by a signal which decreases continuously over time. The signal becomes stable after approximately 30 seconds.

If the liquid in the measuring chamber is now moved along, for instance by means of a pumping or suction device, in such a way that the liquid located in the immediate vicinity is replaced by new liquid of the same sample with the original (non-consumed) $O_2$-content, a measurable rise in the signal can be observed (in a limited time-window of roughly 10 to 20 seconds, see curve a in FIG. 3).

If a gas bubble 11 (e.g., air) adheres to the sensitive region 8 of the sensor 7—as shown in FIGS. 2a and 2b—the decrease of the signal over time t due to $O_2$-consumption, will be significantly smaller than in the case of a bubble-free liquid. The cause of this is the fact that under normal conditions an air bubble contains much more oxygen than the same volume of an aqueous liquid.

The gas bubble 11 will adhere to the sensitive region 8 in spite of the transport of the liquid, which will replace the liquid in the immediate vicinity of the sensor 7 by new liquid. Due to the unchanged amount of $O_2$ supplied by the gas bubble 11 no signal rise will occur (see curve b in FIG. 3).

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A method for detecting the presence or absence of a gas bubble in an aqueous liquid, compromising:
   providing an amperometric sensor positioned within a measuring chamber, wherein said amperometric sensor is configured to determine the concentration of a gaseous component dissolved in said liquid, said amperometric sensor comprising a sensitive region;
   positioning said liquid in said measuring chamber;
   using said amperometric sensor to take at least one first measurement value of said gaseous component from a first portion of said liquid after a predetermined response time, said first portion located in said sensitive region of said sensor;
   moving said liquid along in said measuring chamber without significant pressure change in said liquid, such that a second portion of said liquid within said measuring chamber, which had previously been located outside said sensitive region of said amperometric sensor, is positioned in said sensitive region;
   using said amperometric sensor to take at least one second measurement value of said gaseous component from said second portion of said liquid; and
   detecting the presence or absence of a gas bubble by comparing said first and second measured values, wherein said liquid is free of bubbles in said sensitive region of said amperometric sensor, if said second measured value is higher by a predetermined amount than said first measured value.

2. The method of claim 1, wherein said gas bubble is in at least partial contact with said sensitive region of said amperometric sensor.

3. The method of claim 1 wherein:
   providing an amperometric sensor positioned within a measuring chamber comprises providing said amperometric sensor positioned within a measuring chamber with an open inlet and an open outlet; and
   moving said liquid along in said measuring chamber, without significant pressure change in said liquid, comprises:
      moving said second portion of said liquid to said sensitive region of said sensor in said measuring chamber with said open inlet and said open outlet without significant change in pressure.

4. The method of claim 3, wherein said liquid is moved by a pumping or suction device.

5. The method of claim 1, wherein said gas bubble comprises air.

6. The method of claim 1, wherein said amperometric sensor is a gas sensor.

7. The method of claim 6, wherein said gas sensor is an $O_2$ sensor.

8. The method of claim 1, wherein said aqueous liquid comprises a fluid selected from calibrating fluid, control fluid or sample fluid.

9. The method of claim 8, wherein said sample fluid is a biological fluid.

10. The method of claim 9, wherein said biological fluid is blood.

11. A method for detecting the presence or absence of a gas bubble in an aqueous liquid, compromising:
   providing an amperometric sensor positioned within a measuring chamber, wherein said amperometric sensor is configured to determine the concentration of a gaseous component dissolved in said liquid, said amperometric sensor comprising a sensitive region;
   positioning said liquid in said measuring chamber such that a first portion of said liquid is located in said sensitive region of said sensor;
   using said amperometric sensor to take at least one first measurement value of said gaseous component from said first portion of said liquid after a predetermined response time;
   moving said liquid along in said measuring chamber such that:
      a second portion of said liquid within said measuring chamber, which had previously been located outside said sensitive region of said amperometric sensor is positioned in said sensitive region, and a bubble, if present within said sensitive region of said sensor when taking said at least one first measurement value, does not move from said sensitive region in response to moving said liquid;

using said amperometric sensor to take at least one second measurement value of said gaseous component from said second portion of said liquid; and detecting the presence or absence of a gas bubble by comparing said first and second measured values, wherein said liquid is free of bubbles in said sensitive region of said amperometric sensor, if said second measured value is higher by a predetermined amount than said first measured value.

12. The method of claim 11, wherein providing an amperometric sensor positioned within a measuring chamber further comprises:

providing said amperometric sensor positioned within a measuring chamber with an open inlet and an open outlet.

13. The method of claim 12, wherein moving said liquid along in said measuring chamber, comprises:

moving said second portion of said liquid to said sensitive region of said sensor in said measuring chamber with said open inlet and said open outlet without significant change in pressure.

14. The method of claim 11, wherein said liquid comprises a fluid selected from calibrating fluid, control fluid or sample fluid.

15. The method of claim 14 wherein said sample fluid is a biological fluid.

16. The method of claim 11, wherein detecting the presence or absence of a gas bubble by comparing said first and second measured values comprises:

determining that a bubble is present if said second measured value does not rise compared to said first measured value; and determining that a bubble is not present if said second measured value rises compared said first measured value.

17. A system to detect the presence or absence of a gas bubble in an aqueous liquid, compromising:

an amperometric sensor positioned within a measuring chamber having an open inlet and an open outlet, wherein said amperometric sensor is configured to determine the concentration of a gaseous component dissolved in said liquid, said amperometric sensor comprising a sensitive region, wherein:

said measuring chamber is provided for receiving said liquid; and said amperometric sensor is provided for taking at least one first measurement value of said gaseous component from a first portion of said liquid after a predetermined response time, said first portion located in said sensitive region of said sensor; and at least one of a pump and a suction device, to move said liquid along in said measuring chamber without significant pressure change in said liquid, such that a second portion of said liquid within said measuring chamber, which had previously been located outside said sensitive region of said amperometric sensor, is positioned in said sensitive region; wherein:

said amperometric sensor takes at least one second measurement value of said gaseous component from said second portion of said liquid such that the presence or absence of a gas bubble is detected by comparing said first and second measured values, wherein said liquid is free of bubbles in said sensitive region of said amperometric sensor, if said second measured value is higher by a predetermined amount than said first measured value.

18. The system according to claim 17, wherein said at least one of a pump and a suction device, moves said liquid without causing a significant pressure change in said liquid so that a bubble, if present within said sensitive region of said sensor remains adhered to said sensitive region after moving said liquid.

* * * * *